United States Patent [19]

Lang et al.

[11] Patent Number: 4,588,839

[45] Date of Patent: May 13, 1986

[54] SULPHONAMIDES DERIVED FROM 3-BENZYLIDENE-CAMPHOR AND THEIR APPLICATION AS UV FILTERS

[75] Inventors: Gérard Lang, Saint-Gratien; Alain Malaval, Aulnay-sous-Bois; Gérard Malle, Tremblay-les-Gonesses, all of France

[73] Assignee: L'Oreal, Paris, France

[21] Appl. No.: 511,646

[22] Filed: Jul. 7, 1983

[30] Foreign Application Priority Data

Jul. 8, 1982 [LU] Luxembourg .................... 84264

[51] Int. Cl.[4] .................. C07C 143/78; C07D 303/08; A61K 7/42; A61L 23/00
[52] U.S. Cl. ....................................... 564/84; 424/59; 549/551
[58] Field of Search .................... 564/84; 424/59; 549/551

[56] References Cited

U.S. PATENT DOCUMENTS

| | | | |
|---|---|---|---|
| 2,640,076 | 5/1953 | Ledrut et al. | 260/556 |
| 3,070,443 | 12/1962 | Neugebauer et al. | 564/84 X |
| 3,238,258 | 3/1966 | Daeniker | 564/84 X |
| 4,093,712 | 6/1978 | Okamoto et al. | 564/84 X |
| 4,435,394 | 3/1984 | Ogata et al. | 564/84 X |

FOREIGN PATENT DOCUMENTS

| | | | |
|---|---|---|---|
| 511124 | 11/1953 | Belgium | 260/556 |
| 873299 | 4/1953 | Fed. Rep. of Germany | 260/556 |
| 2237882 | 2/1975 | France | 260/556 |
| 2236515 | 2/1975 | France | 564/84 |
| 2282426 | 3/1976 | France | 564/84 |
| 2309523 | 11/1976 | France | 260/556 |

*Primary Examiner*—Paul F. Shaver
*Attorney, Agent, or Firm*—Fleit, Jacobson, Cohn & Price

[57] ABSTRACT

Compounds having the formula:

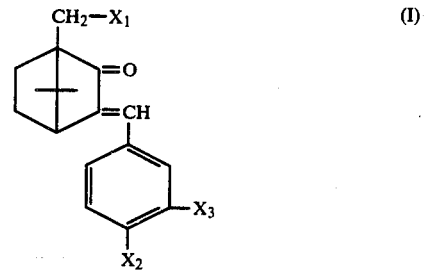

in which $X_1 = H$ or $Y$; $X_2$ is hydrogen, halogen, $C_1$-$C_4$ alkyl or alkoxy, Y or Z; $X_3$ is H, halogen, $C_1$-$C_4$ alkyl or alkoxy, Y or Z; or $X_2$ and $X_3$ together form an alkylidenedioxy containing 1 or 2 C; Y is

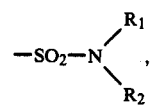

in which $R_1$ is H or $C_1$-$C_4$ alkyl or hydroxyalkyl and $R_2$ is H, alkyl or alkenyl, cycloalkyl, aryl or aralkyl, it being impossible for $R_1$ and $R_2$ to be hydrogen simultaneously; and Z denotes

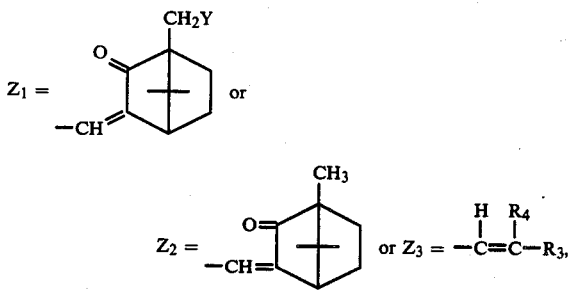

in which $R_3$ is H, —CN or —$COR_5$ and $R_4$ is —$COR_6$, $R_5$ and $R_6$ being $C_1$-$C_{20}$ alkoxy or alkylamino, with the proviso that one of the symbols $X_1$, $X_2$ and $X_3$ is different from the other two and that if $X_1 = H$, $X_2$ and $X_3$ are different from one another and cannot have the meanings $Z_2$ and $Z_3$, one of the two necessarily being Y or $Z_1$; if $X_1$ has the meaning Y, $X_2$ and $X_3$ are different from Y and cannot simultaneously have the meaning $Z_1$, $Z_2$ or $Z_3$ are disclosed for use as UV filters.

17 Claims, No Drawings

SULPHONAMIDES DERIVED FROM 3-BENZYLIDENE-CAMPHOR AND THEIR APPLICATION AS UV FILTERS

The present invention relates to new sulphoamides derived from 3-benzylidene-camphor and to their use as sun filters, in particular in the field of cosmetics.

It is known that light radiation between 280 and 400 nm makes it possible to tan the human epidermis and that rays with a wavelength of between 280 and 320 nm, known by the name UV-B, cause erythema and skin burns, which can hinder the development of the sun tan.

Compounds active in the wavelength region of 280–320 nm are already known; these are 3-benzylidene-camphor derivatives carrying a sulphonic acid group or a metal sulphonate or ammonium sulphonate group in the 10-position of the camphor or in the 3′-position or 4′-position of the benzene nucleus, these compounds being described in French Pat. Nos. 2,282,426 and 2,236,515.

However, although the UV-B rays, with wavelengths of between 280 and 320 nm, play a predominant part in the production of solar erythema and must be filtered out, it is nonetheless true that the UV-A rays, with wavelengths of between 320 and 400 nm, which cuase the skin to tan, are also capable of damaging the skin, in particular in the case of a sensitive skin or a skin continually exposed to solar radiation. It may therefore be advantageous to filter out all the radiation with wavelengths of between 280 and 380 nm.

Furthermore, it is known that the constituents present in cosmetic preparations do not always possess sufficient light stability and that they degrade under the action of light radiation.

Consequently, it is desirable to incorporate, into these preparations, compounds which are capable of filtering out the UV rays and which must have, in addition to good filtering properties, good stability and sufficient solubility in the media normally used in cosmetics, and in particular in oils and fats.

We have discovered that certain sulphonamides derived from 3-benzylidene-camphor are excellent absorbers of ultraviolet radiation in a broad range of wavelengths from 280 to 380 nm.

Furthermore, these compounds have an excellent liposoluble character, a noteworthy light stability and a noteworthy heat stability. These compounds also have the advantage of not being toxic or irritant and of being perfectly harmless to the skin.

The present invention therefore provides sulphonamides derived from 3-benzylidene-camphor, of the general formula:

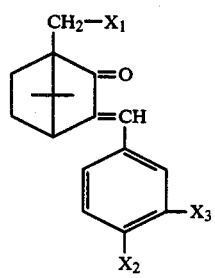

in which $X_1$ denotes a hydrogen atom or the radical Y; $X_2$ denotes a hydrogen or halogen atom, a $C_1$-$C_4$ alkyl or alkoxy radical or a radical Y or Z; $X_3$ denotes a hydrogen or halogen atom, a $C_1$-$C_4$ alkyl or alkoxy radical or a radical Y or Z; or alternatively $X_2$ and $X_3$ together form an alkylenedioxy group in which the alkylene group contains 1 or 2 carbon atoms; Y denotes the group

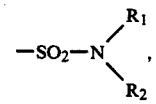

in which $R_1$ denotes a hydrogen atom or a $C_1$-$C_4$ alkyl or hydroxyalkyl radical and $R_2$ denotes a hydrogen atom, a linear or branched alkyl or alkenyl radical or a cycloalkyl, aryl or aralkyl radical, it being possible for these various $C_1$-$C_{20}$ radicals to be substituted by one or more hydroxyl, alkoxy or dialkylamino groups, it being impossible for $R_1$ and $R_2$ simultaneously to denote a hydrogen atom; and Z denotes one of the following groups:

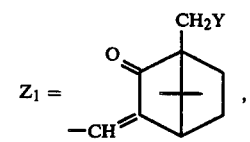

in which Y has the meaning mentioned above, or

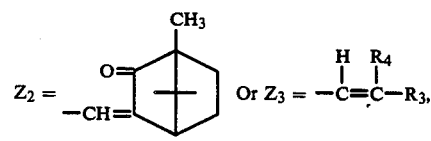

in which $R_3$ denotes a hydrogen atom or a group —CN or —$COR_5$ and $R_4$ denotes a group —$COR_6$, $R_5$ and $R_6$, which are identical or different, being $C_1$-$C_{20}$ alkoxy or alkylamino groups, with the proviso that one of the symbols $X_1$, $X_2$ and $X_3$ is different from the other two and that (a) if $X_1$ denotes a hydrogen atom, $X_2$ and $X_3$ are different from one another and cannot have the meanings $Z_2$ and $Z_3$, one of the two necessarily having the meaning Y or $Z_1$, or (b) if $X_1$ has the meaning Y, $X_2$ and $X_3$ are different from Y and cannot simultaneously have the meaning $Z_1$ or $Z_2$ or $Z_3$.

When $X_1$ denotes a hydrogen atom and $X_3$ has the meaning Y, $X_2$ is preferably different from a hydrogen atom.

The process for the preparation of the compounds of the formula I is typically a two-step process in which the sulphonic acid corresponding to the desired sulphonamide, or an alkali metal salt thereof, is used as the starting material.

The first step consists in preparing the sulphonyl chloride by reacting the starting sulphonic acid or an alkali metal salt thereof with phosphorus pentachloride or thionyl chloride, if appropriate in the presence of an inert solvent such as a chlorinated solvent.

In a second step, a primary or secondary amine

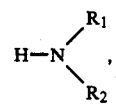

in which $R_1$ and $R_2$ have the meanings mentioned above, is reacted with the sulphonyl chloride in the presence of an inorganic or organic base to take up the hydrochloric acid formed, if appropriate in the presence of an inert solvent such as a chlorinated solvent.

Depending on the nature, of $X_1$, the starting sulphonic acid can be obtained in the following manner:

(a) if $X_1$ denotes a hydrogen atom (1) $X_2$ or $X_3$ denotes Y

The starting sulphonic acid can be prepared as described in French Pat. Nos. 2,282,426 and 2,236,515, in French Patent Application No. 2,237,882 and in French Patent Application No. 2,430,938, that is to say that an aromatic aldehyde is reacted by Haller's method with the sodium salt of camphor in an anhydrous solvent, and sulphonation is then carried out using concentrated $H_2SO_4$, oleum or chlorosulphonic acid.

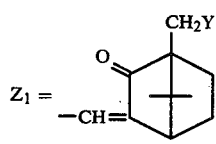

The starting sulphonic acid is prepared according to the reaction scheme:

(α) If $X_2 = Z_1$

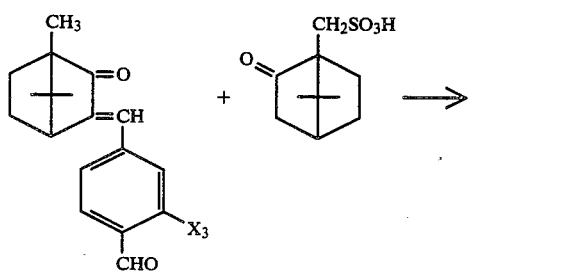

(β) If $X_3 = Z_1$

The same process as above is applied, using the intermediate of the formula:

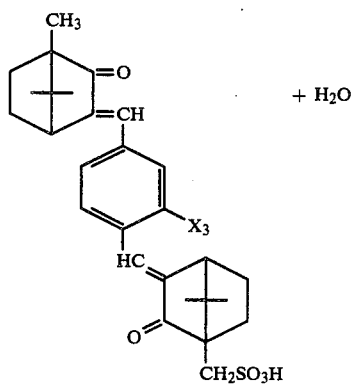

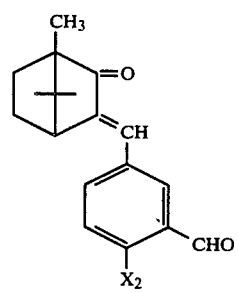

This type of reaction can be carried out in an anhydrous solvent, which is preferably aprotic, in the presence of an organic base such as an alkali metal alcoholate, or an inorganic base such as an alkali metal amide or hydride, the water formed being removed. In certain cases, it is also possible to carry out the reaction in a water-immiscible solvent in the presence of an aqueous solution of sodium hydroxide or potassium hydroxide.

(b) if $X_1$ has the meaning Y four different cases must be considered:

(1) $X_2$ and $X_3$ are different from Y and Z and denote a hydrogen or halogen atom or a $C_1$–$C_4$ lower alkyl or alkoxy group.

In this case, the starting sulphonic acid can be prepared as indicated in French Pat. No. 2,282,426, in French Patent Application No. 2,237,882 and in French Patent Application No. 2,430,938, that is to say that an aromatic aldehyde is reacted with camphosulphonic acid in the presence of a strong base such as sodium methylate.

(2) $X_2$ or $X_3$ has the meaning

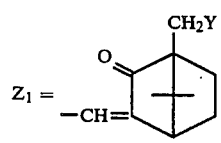

The starting sulphonic acid can be prepared by the processes below:

(α) if $X_3 = Z_1$

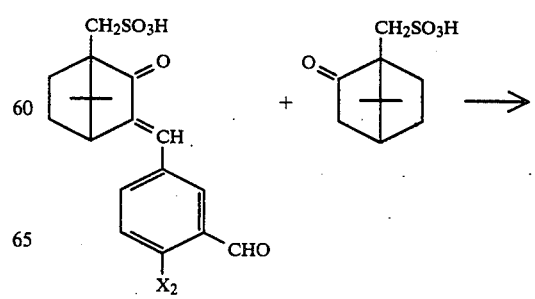

-continued

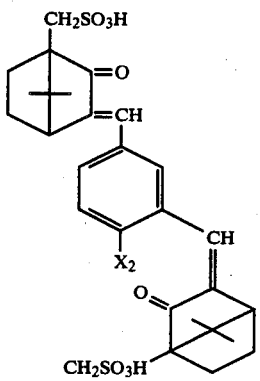

+ H₂O (β) If $X_2=Z_1$

The same process as above is applied, using the intermediate of the formula:

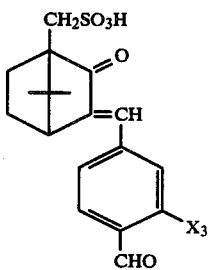

(γ) If $X_3=Z_1$

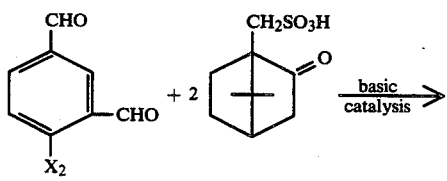

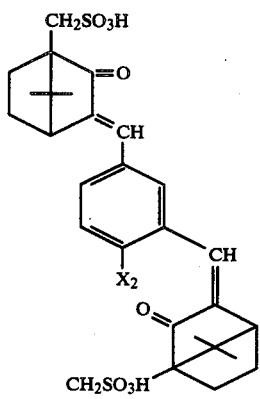

(δ) If $X_2=Z_1$

The same process as above is applied, using the terephthalaldehyde of the formula:

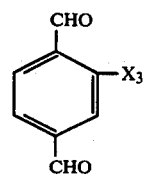

as the intermediate. These reactions (α,β,γ,δ) can be carried out in an anhydrous solvent, which is preferably aprotic, in the presence of an organic base such as an alkali metal alcoholate, or an inorganic base such as an alkali metal amide or hydride, the water formed being removed. In certain cases, it is also possible to carry out the reaction in a water-immiscible solvent in the presence of an aqueous solution of sodium hydroxide or potassium hydroxide.

(3) $X_2$ or $X_3$ has the meaning

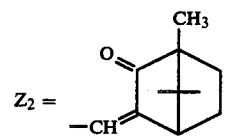

The starting sulphonic acid can be prepared by the processes below:

(α) If $X_3=Z_2$

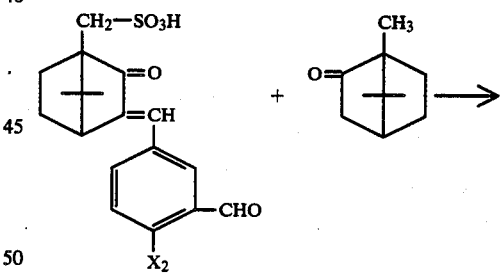

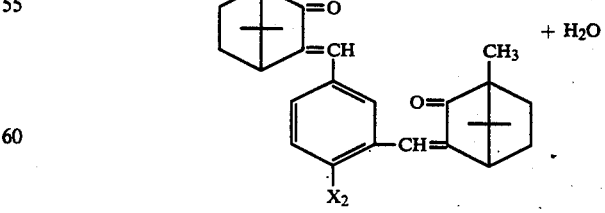

(β) If $X_2=Z_2$

The same process as above is applied, using the intermediate of the formula:

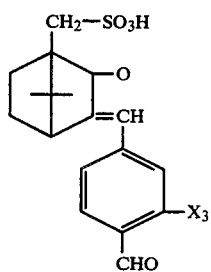

(γ) If $X_3 = Z_2$

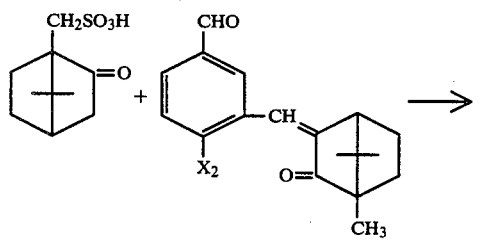

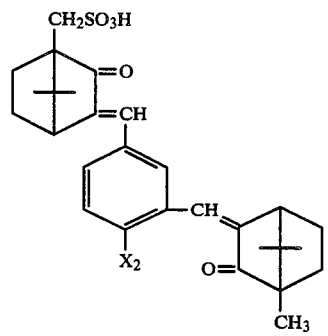

(δ) If $X_2 = Z_2$

The same process as above is applied, using the intermediate of the formula:

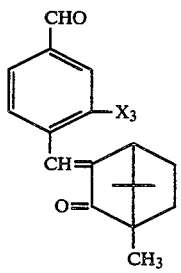

The reactions (α, β, γ, δ) can be carried out in an anhydrous solvent, which is preferably aprotic, in the presence of an organic base such as an alkali metal alcoholate, or an inorganic base such as an alkali metal amide or hydride, the water formed being removed. In certain cases, it is also possible to carry out the reaction in a water-immiscible solvent in the presence of an aqueous solution of sodium hydroxide or potassium hydroxide.

(4) $X_2$ or $X_3$ has the meaning

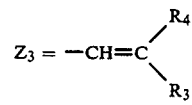

The starting sulphonic acid can be prepared according to the following reaction scheme:

(α) $X_3 = Z_3$

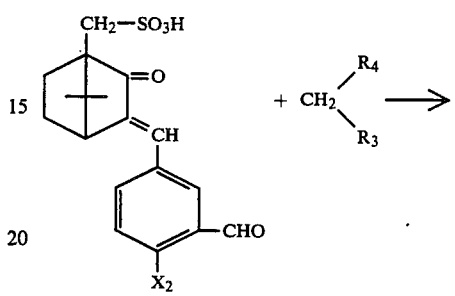

(β) $X_2 = Z_3$

The same process as above is applied, using the intermediate of the formula:

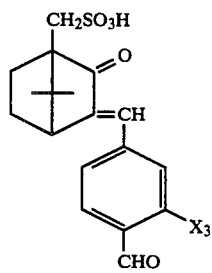

It corresponds to the conventional formation of a cinnamic acid derivative from an aromatic aldehyde and a malonic acid derivative.

The present invention also provides compositions which contain at least one compound of the formula (I) in a cosmetic medium, these can be used as compositions for protecting the human epidermis or as anti-sunburn compositions.

If the compositions according to the invention are used as compositions intended for protecting the human epidermis against ultraviolet rays, they can be presented in a wide variety of forms normally used for this type of composition, and in particular in the form of solutions, lotions, emulsions such as a cream or a milk, or gels, or packaged as aerosols or solid sticks.

They can contain the cosmetic adjuvants normally used in this type of compositions, such as thickeners, softeners, humectants, superfatting agents, emollients, wetting agents, surface-active agents, preservatives, anti-foam agents, perfumes, oils, waxes, dyestuffs and/or pigments serving to colour the composition itself or the skin, or any other ingredient normally used in cosmetics.

The compound of the formula (I) is present, in particular, in an amount by weight of 0.25 to 2%, relative to the total weight of the composition.

A solubilisation solvent which can be used is typically an oil, a wax, a monoalcohol, a polyol or a mixture thereof. The particularly preferred monoalcohols or polyols are ethanol, isopropanol, propylene glycol or glycerol.

In one embodiment the composition is an emulsion in the form of a protecting cream or milk comprising, in addition to the compound of the formula (I), one or more fatty alcohols, oxyethyleneated fatty alcohols, fatty acid esters or fatty acid triglycerides, fatty acids, lanoline, natural and synthetic oils, or waxes, in the presence of water.

Another embodiment consists of lotions such as oily-alcoholic lotions based on lower alcohols such as ethanol, glycols such as propylene glycol and/or polyols such as glycerol, and on fatty acid esters or fatty acid triglycerides.

The cosmetic composition of the invention can also be an oily-alcoholic gel comprising one or more lower alcohols such as ethanol, propylene glycol or glycerol, and a thickener, in the presence of oil.

If the compositions according to the invention are used as anti-sunburn cosmetic compositions, they contain at least one compound of the formula (I), which can optionally be associated with another sun filter specific for UV-B radiation or UV-A radiation. It is thus possible to obtain a formulation which filters out all the UV-B and UV-A rays. The liposoluble filters according to the invention are particularly advantageously used in anti-sunburn compositions because, on account of their non-ionic character, they are compatible both with anionic filters and with cationic filters. This property is very advantageous because an anionic or cationic water-soluble filter can be associated with the liposoluble filter of the invention. Two filtering agents are thus distributed in an emulsion, one in the oily phase and the other in the aqueous phase, and this has the effect of increasing the filtering power of the final composition.

As sun filters which filter out the UV-B rays, there may be mentioned water-soluble filters such as the benzylidene-camphor derivatives described in French Pat. Nos. 2,199,971, 2,236,515, 2,282,426 and 2,383,904, the disclosure of which is hereby incorporated by reference, and more particularly 4-(2-oxo-3-bornylidene-methyl)-phenyltrimethylammonium methyl-sulphate and salts of 4-(2-oxo-3-bornylidene-methyl)-benzenesulphonic acid, of 2-methyl-5-(2-oxo-3-bornylidene-methyl)-benzenesulphonic acid and of 2-phenylbenzimidazole-5-sulphonic acid.

The compounds according to the invention can also be associated with UV-B filters consisting of liposoluble compounds or of oils having filtering properties, such as, in particular, coffee bean oil. As lipophilic UV-B sun filters, there may be mentioned salicylic acid derivatives such as 2-ethylhexyl salicylate and homomenthyl salicylate, cinnamic acid derivatives such as 2-ethylhexyl p-methoxy-cinnamate and 2-ethoxyethyl p-methoxycinnamate, p-amino-benzoic acid derivatives such as amyl p-aminobenzoate and 2-ethylhexyl p-dimethylaminobenzoate, benzophenone derivatives such as 2-hydroxy-4-methoxybenzophenone and 2,2'-dihydroxy-4-methoxybenzophenone, and camphor derivatives such as 3-(4'-methylbenzylidene)-camphor, if appropriate associated with 4-isopropyldibenzoylmethane or 3-benzylidene-camphor.

The compounds according to the invention can also be associated with UV-A filters, amongst which there may be mentioned dibenzoylmethane derivatives such as those described in French Patent Application No. 2,440,933 and German Patent Application No. 2,544,180, the disclosure of which is hereby incorporated by reference.

It is to be understood that the list of sun filters given above which can be used in association with the compounds (I) according to the invention is not exhaustive.

The anti-sunburn compositions according to the invention can be presented in the form of, for example, solutions, lotions, emulsions such as a cream or a milk, oils or fatty or oily-alcoholic gels, or can be packaged as aerosols or solid sticks. They can contain the above-mentioned cosmetic adjuvants normally used in this type of composition.

The anti-sunburn compositions generally contain 0.5 to 15% by weight of compound (I).

The present invention also provides a process for protecting coloured or non-coloured cosmetic compositions which consists in incorporating, into these compositions, an effective amount of at least one compound of the formula (I) as an agent for protection against ultra-violet rays.

These compositions may be, for example, hair compositions such as hair lacquers, setting lotions, which may have a treating or disentangling function, shampoos and colouring shampoos, make-up products such as nail varnishes, treatment creams for the epidermis, make-up foundations and lipsticks, and also any other cosmetic composition which, because of its constituents, can present problems of light stability during storage.

The compounds according to the invention can also be incorporated into various organic materials, and in particular plastics, in order to protect them against ultra-violet radiation. The invention therefore also provides a process for protecting the said organic materials against ultra-violet rays by incorporating at least one compound of formula (I).

This invention is further illustrated by the following Examples.

Examples of compounds (I) according to the invention are the compounds of Examples 1 to 13, of which the method of preparation and various characteristics (appearance, wavelength corresponding to the absorption maximum ($\eta_{max}$), molar absorption coefficient ($\epsilon$) and elementary analysis) are indicated in the table below.

| Example | $X_1$ | $X_2$ | $X_3$ | Procedure | Appearance | UV absorption | Elementary analysis |
|---|---|---|---|---|---|---|---|
| 1 | $-SO_2-NH-CH_2-CH(C_2H_5)(CH_2)_3-CH_3$ | H | H | A | oil | $\lambda max = 295$ nm (Miglyol) ($\epsilon = 20{,}750$) | Theory: C: 69.60 H: 8.58 N: 3.25 S: 7.42 Found: C: 69.68 H: 8.70 N: 3.20 S: 7.29 |
| 2 | $-SO_2NH(CH_2)_3N(CH_3)(CH_3)$ | H | H | A | wax | $\lambda max = 292$ nm ($CH_2Cl_2$) ($\epsilon = 21{,}860$) | Theory: C: 65.34 H: 7.92 N: 6.93 S: 7.92 Found: C: 65.37 H: 7.86 N: 7.00 S: 7.98 |
| 3 | H | $-SO_2NH-CH_2-CH(C_2H_5)(CH_2)_3-CH_3$ | H | B | oil | $\lambda max = 294$ nm ($CH_2Cl_2$) ($\epsilon = 26{,}700$) | Theory: C: 69.60 H: 8.58 N: 3.25 S: 7.42 Found: C: 70.18 H: 8.75 N: 3.24 S: 7.42 |
| 4 | $-SO_2-N(C_6H_5)(C_4H_9)$ | $CH_3$ | H | A | oil | $\lambda max = 304$ nm ($CH_2Cl_2$) ($\epsilon = 21{,}900$) | Theory: C: 72.26 H: 7.53 N: 3.01 S: 6.88 Found: C: 72.25 H: 7.82 N: 2.68 S: 6.34 |
| 5 | H | $-SO_2NH(CH_2)_8CH=CH(CH_2)_7CH_3$ γ | H | B | oil | $\lambda max = 293$ nm ($CH_2Cl_2$) ($\epsilon = 26{,}940$) | Theory: C: 73.81 H: 9.67 N: 2.46 O: 8.44 S: 5.62 |

-continued

| Example | $X_1$ | $X_2$ | $X_3$ | Procedure | Appearance | UV absorption | Elementary analysis |
|---|---|---|---|---|---|---|---|
| 6 | $-SO_2NH \!\!+\!\! CH_2 \!\!\rightarrow\!\!_{15} CH_3$ | H | H | A | wax | $\lambda max =$ 293 nm $(CH_2Cl_2)$ $(\epsilon = 20,348)$ | Found: C: 73.81 H: 9.96 N: 2.17 O: 8.68 S: 5.39 Theory: C: 72.93 H: 9.76 N: 2.57 S: 5.89 Found: C: 72.81 H: 9.75 N: 2.47 S: 5.46 |
| 7 | H | $-SO_2N \begin{matrix} CH_2-CH_2-OH \\ CH_2-CH_2-OH \end{matrix}$ | H | B | oil | $\lambda max =$ 294 nm $(CH_2Cl_2)$ $(\epsilon = 24,230)$ | Theory: C: 61.92 H: 7.13 N: 3.44 S: 7.86 Found: C: 62.34 H: 7.56 N: 3.74 S: 7.31 |
| 8 | H | $CH_3$ | $-SO_2NH-CH_2-CH-(CH_2)_3$ $\quad\quad\quad\quad\quad\; \mid$ $\quad\quad\quad\quad\quad C_2H_5$ $-CH_3$ | B | oil | $\lambda max =$ 290 nm $(CH_2Cl_2)$ $(\epsilon = 20,615)$ | Theory: C: 70.11 H: 8.76 N: 3.15 O: 10.79 S: 7.19 Found: C: 70.30 H: 8.91 N: 2.89 O: 10.83 S: 7.07 |
| 9 | $-SO_2NH \!\!+\!\! CH_2 \!\!\rightarrow\!\!_3 OCH_3$ | $CH_3$ | H | A | white solid melting point = 98–100° C. | $\lambda max =$ 304 nm $(CH_2Cl_2)$ $(\epsilon = 24,900)$ | Theory: C: 65.19 H: 7.65 N: 3.46 O: 15.80 S: 7.90 Found: C: 65.42 H: 7.58 |

-continued

| Example | $X_1$ | $X_2$ | $X_3$ | Procedure | Appearance | UV absorption | Elementary analysis |
|---|---|---|---|---|---|---|---|
| | | | | | | | N: 3.94<br>O: 15.62<br>S: 7.61 |
| 10 | $-SO_2NH-CH_2-CH-$<br>$\quad\quad\quad\quad\quad\quad\quad\quad\; \mid$<br>$\quad\quad\quad\quad\quad\quad\quad\; C_2H_5$<br>$-(CH_2)_3-CH_3$ | $OCH_3$ | H | A | oil | $\lambda max =$<br>320 nm<br>$(CH_2Cl_2)$<br>$(\epsilon = 25,000)$ | Theory:<br>C: 67.68<br>H: 8.46<br>N: 3.04<br>O: 13.88<br>S: 6.94<br>Found:<br>C: 68.01<br>H: 8.41<br>N: 3.42<br>O: 13.56<br>S: 6.60 |
| 11 | H | $CH_3$ | $SO_2NH-C_2H_5$ | B | white solid melting point = 148–150° C. | $\lambda max =$<br>290 nm<br>$(CH_2Cl_2)$<br>$(\epsilon = 21,760)$ | Theory:<br>C: 66.48<br>H: 7.48<br>N: 3.88<br>O: 13.30<br>S: 8.86<br>Found:<br>C: 66.64<br>H: 7.62<br>N: 4.01<br>O: 13.32<br>S: 8.41 |
| 12 | $-SO_2-NH-CH_2-$<br>$-CH-(CH_2)_3-CH_3$<br>$\; \mid$<br>$\; C_2H_5$ | 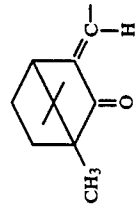 | H | C | pale yellow solid melting point 75° C. | $\lambda max =$<br>340 nm<br>$(CH_2Cl_2)$<br>$(\epsilon = 37,700)$ | Theory:<br>C: 72.85<br>H: 8.60<br>N: 2.36<br>O: 10.79<br>S: 5.40<br>Found:<br>C: 73.01<br>H: 8.55<br>N: 2.42<br>O: 10.70<br>S: 5.25 |

-continued

| Example | $X_1$ | $X_2$ | $X_3$ | Procedure | Appearance | UV absorption | Elementary analysis |
|---|---|---|---|---|---|---|---|
| 13 | $-SO_2-NH-CH_2-$<br>$-CH-(CH_2)_3-CH_3$<br>$\quad\|$<br>$\quad C_2H_5$ | structure with bicyclic ring, $SO_2-NH-CH_2-CH(C_2H_5)-(CH_2)_3-CH_3$ substituent and $-C(=O)-H$ group | H | D | pale yellow solid melting point = 165° C. | $\lambda_{max} =$ 342 nm $(CH_2Cl_2)$ $(\epsilon = 41,000)$ | Theory:<br>C: 67.35<br>H: 8.67<br>N: 3.57<br>O: 12.24<br>S: 8.16<br>Found:<br>C: 67.40<br>H: 8.55<br>N: 3.21<br>O: 12.67<br>S: 7.70 |

Miglyol: triglycerides of $C_8$-$C_{12}$ fatty acids

The procedures A to D used for the preparation of the compounds of Examples 1 to 13 are set out below.

PROCEDURE A (1) Preparation of the sodium salt of 3-benzylidene-10-camphosulphonic acid 348 g of camphosulphonic acid, 80 ml of methanol and 2 liters of anhydrous toluene are introduced into a 4 liter reactor and 167 g of sodium methylate are then added rapidly, with stirring.

The exothermic mixture warms up and is kept at 85°–90° C. for 30 minutes.

It is then cooled to 65° C., 159 g of benzaldehyde are introduced dropwise (about 40 minutes) and the mixture is heated under reflux for 3 hours.

The reaction mixture is then cooled and poured into 3 liters of vigorously stirred water, and the precipitate formed is filtered off, washed with water and dried in vacuo to give 334 g of the expected compound (yield=65%).

(2) Preparation of 3-benzylidene-10-camphosulphonyl chloride 330 g of the above compound and 208 g of phosphorus pentachloride are introduced into a 2 liter reactor.

The solid mixture is heated to 80° C., with stirring, until it solidifies. The solid is then hydrolysed, filtered off, washed several times with cold water and dried in vacuo.

This gives 303 g of the expected compound (yield=93%).

Determination of the chlorine by AgNO$_3$: 2.98 milliequivalents/g (theory: 2.95 milliequivalents/g).

(3) Preparation of N-(2-ethylhexyl)-3-benzylidene-10-camphosulphonamide 300 g of the above acid chloride, 2 liters of anhydrous methylene chloride, 115 g of 2-ethylhexylamine (or 0.9 mol of one of the amines used in the preparation of the examples in the table) and 225 g of triethylamine are introduced into a 4 liter reactor.

The reaction mixture is kept under reflux for 1 hour.

The triethylamine hydrochloride is filtered off and the organic phase is washed with water, dilute hydrochloric acid and water again, dried and concentrated in vacuo.

The product is then dried at 100° C. in vacuo to give 334 g of a thick oil corresponding to the expected product (yield=87%).

The sodium salt of 3-(p-methyl- or p-methoxy-benzylidene)-10-camphosulphonic acid is used as the starting material to prepare the compounds of Examples 4, 9 and 10.

PROCEDURE B (1) Preparation of 4-(3'-methylidene-camphor)-benzenesulphonyl chloride 40 g of the sodium salt of 4-(3'-methylidene-camphor)-benzenesulphonic acid and 12 g of phosphorus pentachloride are introduced into a 1 liter reactor.

The powdery mixture is heated at 80° C., with stirring, until it solidifies.

After it has returned to ambient temperature, 300 ml of iced water are added. The solid is withdrawn from the reactor, ground, washed several times with cold water and then dried in vacuo at ambient temperature.

This gives 39.4 g of the expected acid chloride (yield=99%).

Determination of the chlorine by AgNO$_3$: 2.97 milliequivalents/g (theory=2.95 milliequivalents/g)

(2) Preparation of N-(2-ethylhexyl)-4-(3'-methylidene-camphor)-benzenesulphonamide 39 g of the above acid chloride, 300 ml of anhydrous methylene chloride, 15.4 g of 2-ethylhexylamine (or 0.11 mol of one of the amines used in the preparation of the examples in the table) and 40 ml of triethylamine are introduced into a 1 liter reactor.

The reaction mixture is kept under reflux for 1 hour.

The triethylamine hydrochloride is then filtered off and the organic phase is washed with water, dilute hydrochloric acid and water again, dried and concentrated in vacuo.

The product is dried in vacuo at 100° C. to give 44.9 g of the expected product (yield=89%).

The sodium salt of 2-methyl-5-(3'-methylidene-camphor)-benzenesulphonic acid is used as the starting material to prepare the compounds of Examples 8 and 11.

PROCEDURE C (1) Preparation of 3,3'-terephthalylidene-10-dicamphosulphonic acid 134 g of 4'-formyl-3-benzylidene-camphor, 1,350 ml of dry toluene, 116 g of 10-d,1-dicamphosulphonic acid and 22 g of sodium hydroxide pellets are placed in an equipped 3 liter three-necked round-bottomed flask.

The mixture is heated under reflux for 1 hour, the water formed being separated off using a Dean-Stark apparatus (18 ml). The solution is cooled and poured into 3 liters of isopropyl ether. The precipitate is filtered off, washed with isopropyl ether and dried.

The compound obtained is dissolved in 2 liters of hot acetone and acidified with 25 ml of concentrated hydrochloric acid. The inorganic salts which precipitate are filtered off and the filtrate is evaporated to dryness. The residue is taken up in 1 liter of isopropyl ether, filtered off and dried in vacuo. This gives 191 g of the desired compound (yield=79%).

(2) Preparation of 3,3'-terephthalylidene-10-dicamphosulphonyl chloride 120 g (0.249 mol) of 3,3'-terephthalylidene-10-dicamphosulphonic acid and 57 g of phosphorus pentachloride are introduced into a 1 liter reactor. The mixture is heated in an oilbath to 140° C. and then 180° C. The reaction mixture becomes syrupy. It is poured into a mortar. After cooling and grinding, ice is added. The product is filtered off, washed with water and dried. This gives 122 g of the acid chloride.

(3) Preparation of N-(2-ethylhexyl)-3,3'-terephthalylidene-10-dicamphosulphonamide 500 cm$^3$ of dry methylene chloride and 50 g of the acid chloride obtained above are introduced into a 1 liter reactor. 16.3 cm$^3$ of 2-ethylhexylamine and then 15.1 g of triethylamine are added. The temperature is kept at between 25° and 30° C. for 2 hours and the reaction mixture is then poured into 300 cm$^3$ of water. The organic phase obtained is washed with 1N hydrochloric acid and then with water until the pH of the washings is 6–7. After drying over sodium sulphate, the product is purified by chromatography on a silica column, methylene chloride being used as the solvent.

This gives 30 g of a pale yellow solid product after evaporation of the solvent.

PROCEDURE D (1) Preparation of 3,3'-terephthalylidene-10,10'-dicamphosulphonic acid 223 g (2 mols) of 97% pure sodium methylate are added to a suspension of 464.8 g (2 mols) of 10-d,1-camphosulphonic acid in 4 liters of toluene and 0.2 liter of methanol, and the mixture is then heated under reflux for 30 minutes.

A solution of 134.2 g (1 mol) of terephthalaldehyde in 1 liter of a 90/10 mixture of toluene/methanol is then added under nitrogen over a period of 2 hours. The mixture is kept under reflux for 1 hour and then cooled to ambient temperature.

The toluene is drawn off and the product is taken up in 1.5 liters of water and 1.5 liters of 35% strength hydrochloric acid. The mixture is heated under reflux for 1 hour, the residual toluene being distilled.

After the medium has been concentrated and cooled, the product is filtered off, washed with 6N hydrochloric acid and dried in vacuo at 80° C. and then at 100° C. This gives 395 g of the desired compound.

(2) Preparation of 3,3'-terephthalylidene-10,10'-dicamphosulphonyl dichloride 90 g (0.16 mol) of 3,3'-terephthalylidene-10,10'-dicamphosulphonic acid and 66.6 g of phosphorus pentachloride are introduced into a 1 liter reactor. The mixture is stirred for 2 hours at 60°–65° C. and 37 g of phosphorus pentachloride are then added. The heating is continued for a further 3 hours and the mixture is then left to return to ambient temperature.

The reaction mixture is run slowly into a mixture of ice and water. The product is filtered off and then washed with water and dried. This gives 90 g of the acid dichloride.

(3) Preparation of di-N-(2-ethylhexyl)-3,3'-terephthalylidene-10,10'-dicamphosulphonamide 500 cm³ of dry methylene chloride and 89 g of the acid dichloride obtained above are introduced into a 1 liter reactor. 50 cm³ of 2-ethylhexylamine are added. The reaction mixture becomes homogeneous. 84 cm³ of triethylamine are run in dropwise. After a reaction time of 1 hour, the triethylamine hydrochloride is filtered off. The organic phase is washed with 1N hydrochloric acid until the pH of the washings is acid, and then with five times 500 cm³ of water. After the organic phase has been dried, the disulphonamide is obtained by evaporation of the solvent. This gives 78 g of a pale yellow solid product.

The filters (I) according to the invention can be introduced into the following cosmetic compositions.

EXAMPLE 14

Sun cream

| | |
|---|---|
| Compound of Example 1 | 3 g |
| 4-(2-Oxo-3-bornylidene-methyl)-phenyl-trimethylammonium methyl-sulphate | 2 g |
| Polyoxyethyleneated fatty alcohols | 7 g |
| Fatty acid triglycerides | 30 g |
| Glycerol monostearate | 2 g |
| Silicone oil | 1.5 g |
| Cetyl alcohol | 1.5 g |
| Preservative, perfume q.s. | |
| Demineralised water q.s.p. | 100 g |

This emulsion is prepared by the customary techniques, the compound of Example 1 being dissolved in the fatty phase and the 4-(2-oxo-3-bornylidene-methyl)-phenyltrimethylammonium methyl-sulphate being dissolved in the aqueous phase.

EXAMPLE 15

Oily-alcoholic sun lotion

The following compounds are mixed, conveniently with heating to about 40°–45° C. in order to homogenise them:

| | |
|---|---|
| Compound of Example 2 | 4 g |
| 96° strength ethanol | 47.5 g |
| Perfume q.s. | |
| Triglycerides of $C_8$–$C_{12}$ fatty acids q.s.p. | 100 g |

EXAMPLE 16

Greasy sun gel

| | |
|---|---|
| Compound of Example 3 | 2.5 g |
| 4-Methoxy-4'-tert.-butyldibenzoylmethane sold under the name "PARSOL 1789" by GIVAUDAN | 1.5 g |
| Cacao butter | 5 g |
| Antioxidant | 0.05 g |
| Silica | 10 g |
| Triglycerides of $C_8$–$C_{12}$ fatty acids q.s.p. | 100 g |

This gel is obtained by heating the fatty substances to about 40°–45° C. and then by adding the silica, with vigorous stirring, and finally the filters.

The compound of Example 3 can be replaced by the compound of Example 8.

EXAMPLE 17

Sun oil

The following ingredients are mixed, conveniently with heating to about 40°–45° C. in order to homogenise them:

| | |
|---|---|
| Compound of Example 5 | 5 g |
| Cacao butter | 2.5 g |
| Antioxidant, perfume q.s. | |
| Triglycerides of $C_8$–$C_{12}$ fatty acids q.s.p. | 100 g |

EXAMPLE 18

Sun milk

| | |
|---|---|
| Compound of Example 6 | 2 g |
| Compound of Example 10 | 1.5 g |
| Cetyl-stearyl alcohol | 2 g |
| Cetyl alcohol | 2 g |
| Triglycerides of $C_8$–$C_{12}$ fatty acids | 20 g |
| Lanoline | 4 g |
| Stearic acid | 0.5 g |
| Silicone oil | 0.3 g |
| Carbopol 934 (crosslinked polyacrylic acid sold by GOODRICH CHEMICAL) | 0.15 g |
| Triethanolamine | 0.2 g |
| Preservative, perfume q.s. | |
| Demineralised water q.s.p. | 100 g |

This sun milk is prepared in the same way as the sun cream of Example 14.

EXAMPLE 19

Protecting day cream

| | |
|---|---|
| Compound of Example 1 | 0.5 g |
| PARSOL 1789 | 0.3 g |

-continued

| | |
|---|---|
| Triglycerides of $C_8$–$C_{12}$ fatty acids | 31 g |
| Glycerol monostearate | 6 g |
| Stearic acid | 2 g |
| Cetyl alcohol | 1.2 g |
| Lanoline | 4 g |
| Propanediol | 2 g |
| Triethanolamine | 0.5 g |
| Preservatives, perfume q.s. | |
| Demineralised water q.s.p. | 100 g |

This composition is prepared in the same way as the sun cream of Example 14.

The compound of Example 1 can be replaced by the compounds of Examples 10 or 11.

EXAMPLE 20

Protecting day cream

| | |
|---|---|
| Self-emulsifiable glycerol stearate | 3 g |
| Cetyl alcohol | 0.5 g |
| Stearyl alcohol | 0.5 g |
| Vaseline oil | 12 g |
| Sesame oil | 10 g |
| Stearic acid | 3 g |
| Compound of Example 1 | 1 g |
| Glycerol | 5 g |
| Methyl para-hydroxybenzoate | 0.3 g |
| Demineralised water q.s.p. | 100 g |

EXAMPLE 21

Protecting moisturising cream

| | |
|---|---|
| Magnesium lanolate | 3 g |
| Lanoline alcohol | 5 g |
| Vaseline oil | 27 g |
| Vaseline | 15 g |
| Compound of Example 1 | 2 g |
| Preservatives | q.s. |
| Perfume | q.s. |
| Demineralised water q.s.p. | 100 g |

EXAMPLE 22

Protecting hand cream

| | |
|---|---|
| Tween 60 (Atlas) = sorbitan monolaurate oxyethyleneated with 20 mols of ethylene oxide | 2 g |
| Cetyl alcohol | 1 g |
| Isopropyl myristate | 3 g |
| Vaseline oil | 7 g |
| Silicone oil | 7 g |
| Compound of Example 5 | 2 g |
| Carbopol 940 (Goodrich Chemical) | 0.3 g |
| Triethanolamine | 0.3 g |
| Preservatives | q.s. |
| Perfume | q.s. |
| Demineralised water q.s.p. | 100 g |

EXAMPLE 23

Protecting day cream

| | |
|---|---|
| Compound of Example 12 | 0.5 g |
| Compound of Example 1 | 0.5 g |
| Self-emulsifiable glycerol stearate | 3 g |
| Cetyl alcohol | 0.5 g |
| Stearyl alcohol | 0.5 g |
| Vaseline oil | 12 g |
| Sesame oil | 10 g |

-continued

| | |
|---|---|
| Stearic acid | 3 g |
| Glycerol | 5 g |
| Methyl para-hydroxybenzoate | 0.3 g |
| Demineralised water q.s.p. | 100 g |

EXAMPLE 24

Protecting moisturising cream

| | |
|---|---|
| Compound of Example 13 | 0.8 g |
| 3-(4'-Methylbenzylidene)-camphor | 0.5 g |
| Magnesium lanolate | 3 g |
| Lanoline alcohol | 5 g |
| Vaseline oil | 27 g |
| Vaseline | 15 g |
| Preservatives and perfume q.s. | 15 g |
| Demineralised water q.s.p. | 100 g |

We claim:

1. A sulphonamide compound having the general formula:

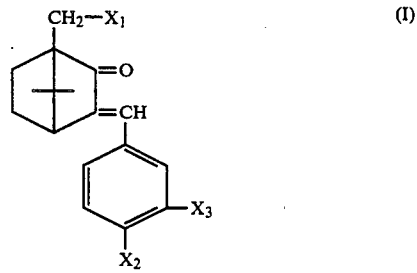 (I)

in which $X_1$ denotes a hydrogen atom or the radical Y; $X_2$ denotes a hydrogen or halogen atom, a $C_1$–$C_4$ alkyl or alkoxy radical or a radical Y or Z; $X_3$ denotes a hydrogen or halogen atom, a $C_1$–$C_4$ alkyl or alkoxy radical or a radical Y or Z; or alternatively $X_2$ and $X_3$ together form an alkylenedioxy group containing 1 or 2 carbon atoms; Y denotes the radical

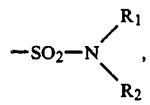

in which $R_1$ denotes a hydrogen atom or a $C_1$–$C_4$ alkyl or hydroxyalkyl radical; $R_2$ denotes a hydrogen atom, or a linear or branched alkyl, alkenyl, cycloalkyl, aryl or aralkyl radical, said radical containing 1 to 20 carbon atoms and it being possible for it to be substituted by one or more hydroxyl, alkoxy or dialkylamino groups, with the proviso that $R_1$ and $R_2$ do not simultaneously denote a hydrogen atom; and Z denotes a group;

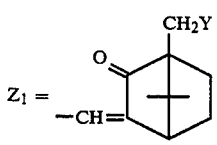

in which Y is as defined above or

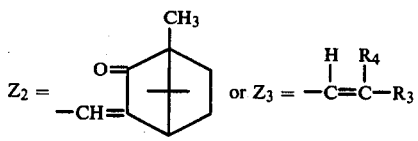

in which $R_3$ denotes a hydrogen atom or a radical —CN or —$COR_5$ and $R_4$ denotes a radical —$COR_6$, in which radicals $R_5$ and $R_6$, which are identical or different, denote $C_1$–$C_{20}$ alkoxy or alkylamino groups, with the proviso that one of the symbols $X_1$, $X_2$ and $X_3$ is different from the other two and that (a) if $X_1$ denotes a hydrogen atom, $X_2$ and $X_3$ are different from one another and are not $Z_2$ or $Z_3$, one of the two necessarily being Y or $Z_1$, or (b) if $X_1$ is Y, $X_2$ and $X_3$ are different from Y and are not simultaneously $Z_1$ or $Z_2$ or $Z_3$.

2. A compound according to claim 1, in which $X_1$ denotes a hydrogen atom, $X_3$ is a radical Y, and $X_2$ is other than a hydrogen atom.

3. A compound according to claim 1, in which $X_1$ is a radical Y, $X_2$ denotes a hydrogen atom or a methyl or methoxy radical and $X_3$ denotes a hydrogen atom.

4. A compound according to claim 3, selected from the group consisting of N-(2-ethylhexyl)-3-benzylidene-10-camphosulphonamide, N-3-(N',N'-dimethylamino)-propyl-3-benzylidene-10-camphosulphonamide, N-hexadecyl-3-benzylidene-10-camphosulphonamide, N-phenyl-N-n-butyl-3-(4'-methyl)-benzylidene-10-camphosulphonamide, N-(3-methoxypropyl)-3-(4'-methyl)-benzylidene-10-camphosulphonamide and N-(2'-ethylhexyl)-3-(4'-methoxy)-benzylidene-10-camphosulphonamide.

5. A compound according to claim 1 in which $X_1$ denotes a hydrogen atom, $X_2$ is a radical Y and $X_3$ is a hydrogen atom.

6. A compound according to claim 5, selected from the group consisting of N-(2-ethylhexyl)-4-(3'-methylidene-camphor)-benzenesulphonamide, N-(9-octadecylen-1-yl)-4-(3'-methylidene-camphor)-benzenesulphonamide and N,N-(2-hydroxyethyl)-4-(3'-methylidene-camphor)-benzenesulphonamide.

7. A compound according to claim 2, in which $X_1$ denotes a hydrogen atom, $X_3$ is a radical Y and $X_2$ denotes a methyl group.

8. A compound according to claim 7, selected from the group consisting of N-(2-ethylhexyl)-3-(3'-methylidene-camphor)-benzenesulphonamide and N-ethyl-3-(3'-methylidene-camphor)-benzenesulphonamide.

9. A compound according to claim 1, in which $X_1$ is a radical Y, $X_2$ is a radical $Z_1$ or $Z_2$ and $X_3$ is a hydrogen atom.

10. A compound according to claim 9, selected from the group consisting of N-(2-ethylhexyl)-3,3'-terephthalylidene-10-dicamphosulphonamide and di-N-(2-ethylhexyl)-3,3'-terephthalylidene-10,10'-dicamphosulphonamide.

11. A composition suitable for use in cosmetics which contains an effective amount of at least one compound as defined in claim 1 as an agent for protection against UV rays, in a cosmetically acceptable medium.

12. A composition according to claim 11, which is in the form of an anti-sunburn composition, and contains 0.5 to 15% by weight of a said compound.

13. A composition according to claim 12, which also contains at least one other water-soluble or liposoluble sun filter having a filtering action towards the UV-B rays, or a sun filter which filters out the UV-A rays.

14. A cosmetic composition according to claim 11, which is in the form of a composition for protecting the human epidermis, and which contains 0.25 to 2% by weight of a said compound.

15. A composition according to claim 11 which contains at least one cosmetic adjuvant which is a thickener, softener, superfatting agent; emollient, humectant, wetting agent, surface-active agent, preservative, antifoam agent, perfume, oil, wax, dyestuff or pigment.

16. Process for protecting the human epidermis against ultraviolet rays, which comprises applying thereto an effective amount of at least one compound of formula (I) as defined in claim 1.

17. Process for protecting a cosmetic composition against UV rays, which comprises incorporating therein a effective amount of at least one compound of the formula (I) as defined in claim 1.

* * * * *